(12) United States Patent
Kiso et al.

(10) Patent No.: US 6,503,885 B1
(45) Date of Patent: Jan. 7, 2003

(54) CARBOXYMETHYLGALACTOSE DERIVATIVES

(75) Inventors: Makoto Kiso, Gifu (JP); Hideharu Ishida, Gifu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/787,610

(22) PCT Filed: Sep. 17, 1999

(86) PCT No.: PCT/JP99/05098

§ 371 (c)(1),
(2), (4) Date: Mar. 20, 2001

(87) PCT Pub. No.: WO00/17216

PCT Pub. Date: Mar. 30, 2000

(30) Foreign Application Priority Data

Sep. 21, 1998 (JP) ............................................. 10-265973

(51) Int. Cl.[7] .......................... A61K 31/70; C07H 3/06; C07H 15/04
(52) U.S. Cl. ............................. 514/25; 514/23; 514/61; 536/4.1; 536/18.5
(58) Field of Search .............................. 514/23, 25, 61; 536/4.1, 18.5

(56) References Cited

U.S. PATENT DOCUMENTS

| | | |
|---|---|---|
| 4,952,683 A | 8/1990 | Tschannen |
| 5,589,465 A | 12/1996 | Ishida |
| 5,869,460 A | 2/1999 | Usui |

FOREIGN PATENT DOCUMENTS

| | | |
|---|---|---|
| JP | 60-197697 | 10/1985 |
| JP | 8-99989 | 4/1996 |
| JP | 9-183789 | 7/1997 |
| JP | 10-25252 | 1/1998 |

OTHER PUBLICATIONS

Ishida et al, *Carbohydrate Research*, 303:131–133 (1997).

*Primary Examiner*—Samuel Barts
(74) *Attorney, Agent, or Firm*—Sughrue Mion, PLLC

(57) ABSTRACT

Carboxymethylgalactose derivatives represented by general formula (1);

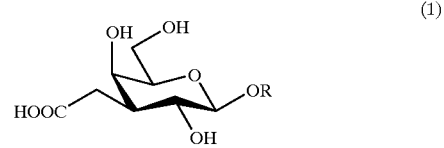

and salts thereof, which exhibit reactivity to selectins and are useful as inhibitors against selectin-related diseases such as various inflammations and cancerous metastasis; In said formula, R is a group rep resented by formula (1a), (1b) or (1c).

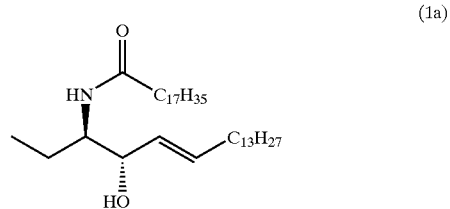

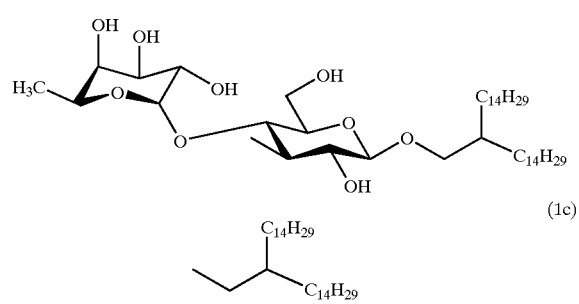

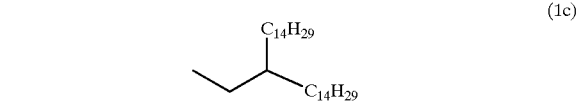

35 Claims, No Drawings

CARBOXYMETHYLGALACTOSE DERIVATIVES

This application is the National Phase application of PCT/JP99/05098, filed Sep. 17, 1999.

TECHNICAL FIELD

The present invention relates to carboxymethylgalactose derivatives, more specifically carboxymethylgalactose derivatives acting as ligands which bind to a cell adhesion molecule, i.e., selectin, and are useful for treating and preventing various selectin-related diseases such as inflammations and cancerous metastasis.

BACKGROUND ART

It has been noted that the interactions between a selectin, specifically, E-selectin (ELAM-1), P-selectin (GMP-140) or L-selectin (LECAM-1) and sugar chains are associated with various diseases. The above LECAM-1 is an adhesive molecule expressed mainly on leukocytes; ELAM-1 is a cell adhesion molecule expressed mainly on vascular endothelial cells; and GMP-140 is an adhesive molecule mainly expressed on thrombocyte cells.

In cancer cells and spinal cells, sialyl Lewis-a (SLe$^a$) or sialyl Lewis-x(SLe$^x$) having L-fucose in its molecule appears, and it is specifically recognized by leukocyte adhesion factor (L- or E-selectin) which appears on the surface of vascular endothelial cells stimulated with interleukin-1 (IL-1) or tumor necrosis factor (TNF) (e.g., Science, Vol. 258, p 964–969, 1992). That is, the cancer cells and myeloid cells, which express SLe$^a$ or SLe$^x$ on the surface thereof, bind to the vascular endothelial cells.

Incidentally, human thrombocytes and vascular endothelial cells activated by the thrombin express P-selectin which also sharply recognizes SLe$^a$ or SLe$^x$. Therefore, the human thrombocytes and vascular endothelial cells bind to neutrophils and monocyte which express these sugar chains on the surface of the cells (Science, Vol. 258, p 964–969, 1992). It is thought that these phenomena are associated with the progress of inflammation, cancer metastasis, thrombus and other circulatory diseases.

Thus, proposed are various measures to inhibiting selectin-related inflammation, cancer metastasis and the like by blocking the binding of these selectins to SLe$^a$ or SLe$^x$ to interrupt the adhesion of the selectin-expression cells to cancer cells, leukocyte cells and thrombocytes (e.g., U.S. Pat. Nos. 5,817,742, 5,648,344 and 5,837,689, European Patent Publications (WO) Nos. 9202527, 9929705, 9731007 and 9731625). Particularly for complicated diseases, a blocker which can bind to various selectins to inhibit cell adhesion is desirable.

Since the SLe$^x$ was reported for the first time as a ligand for ELAM-1, several SLe$^x$ derivatives are reported. These derivatives are acidic oligosaccharides and have a sialic acid moiety. Also reported are a number of SLe$^x$ derivatives which consist of oligosaccharide having a carboxymethyl group or a sulfonate group in place of the sialic acid moiety of the acidic oligosaccharides (e.g., Carbohydrate Research, vol. 303, p 131–133, 1997 and Japanese Unexamined Patent Publication No. 1996-99989).

However, no report has been published on SLe$^a$ derivatives which consist of oligosaccharide having a carboxymethyl group, or on sulfatide derivatives having a carboxymethylgalactosyl moiety in place of the sulfogalactosyl moiety.

It is reported that SLe$^x$ and SLe$^a$ are common ligands for ELAM-1, GMP-140 and LECAM-1, whereas sulfatides have a binding specific for GMP-140 and LECAM-1 and thus are ligands for these GMP-140 and LECAM-1, and also have anti-inflammatory actions (International Immunology, vol. 8, p 1905–1913, 1996).

An object of the present invention is to provide an SLe$^a$ derivative which functions as a ligand having affinity for various selectins in the selectin family, particularly a novel glycolipid derivative whose sialic acid portion is replaced by carboxymethylgalalctose and a novel sulfatide derivative having carboxymethlylgalactosyl group as a substituent for sulfogalactosyl group.

The inventors have conducted extensive research in order to provide an SLe$^a$ analog (especially that which more strongly binds to selectins and blocks their cellular adhesiveness) serving as a ligand for selectins. Consequently, the inventors succeeded in synthesizing a novel glycolipid derivative prepared by substituting the sialic acid portion of the SLe$^a$ with carboxymethylgalactose and a novel sulfatide derivative having similar carboxymethylgalactosyl group, which were found to achieve the above object. The present invention was accomplished based on these findings.

DISCLOSURE OF INVENTION

The present invention provides carboxymethylgalactose derivatives represented by the formula (1);

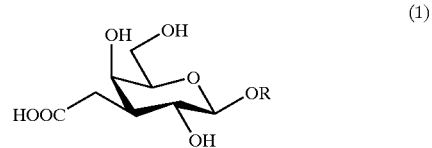

(1)

and its salts, wherein R represents the following group (1a), (1b) or (1c)

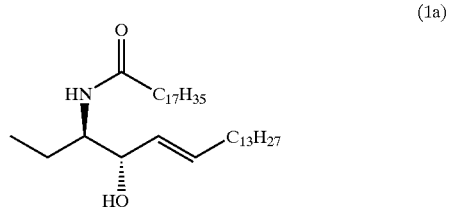

(1a)

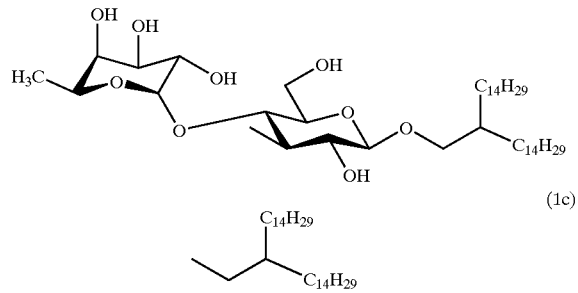

(1b)

(1c)

The compounds of the present invention have reactivity to the selecting, ELAM-1, GMP-140 and LECAM-1. Therefore, as a ligand with selecting, the compound inhibits the cell adhesion of these selectins and is useful for treating and preventing various selectin-related diseases. For example, the compound is useful for inhibiting various inflammations, cancer metastasis, etc.

Preparation of the compound of the invention will be described in detail below. The compound of the invention represented by the formula (1) can be prepared by various methods. Particularly, the compound of the invention can be easily prepared by the methods shown in the reaction formula (I)–(IV) below. In the reaction formulas and their explanations below, the following abbreviations are used.

Bz: Benzoyl group,
Bn: Benzyl group,
Me: Methyl group,
SE: 2-(Trimethylsilyl)ethyl group,
TBDPS: t-Butyldiphenylsilyl group,
TMSOTf: Trimethylsilyltrifluoromethanesulfonate,
TfOH: Trifluoromethanesulfonic acid,
$Ph_3P$: Triphenylphosphine,
TBAF: Tetrabutylammoniumfluoride,
WSC: Water-soluble carbodiimide,
$NaBH_3CN$: Sodium cyanoborohydride,
TFA: Trifluoroacetic acid,
DBU: 1,8-Diazabicyclo-[5,4,0]-7-undecene,
$Cl_3CCN$: Trichloroacetonitrile The compound of the invention represented by the formula (1) in which R is the group (1a) can be prepared by the method shown in the reaction formula (I) below.

Reaction formula (I)

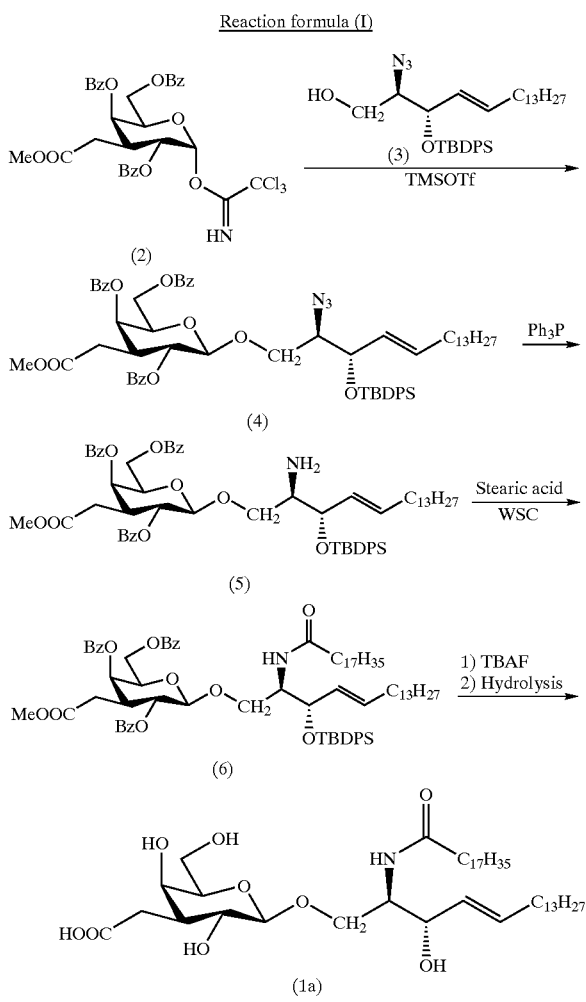

According to the above reaction formula (I), a compound (4) can be prepared by the following procedure. In an inert solvent, e.g., methylene chloride and the like, are dissolved the known compound (2) (Carbohydrate Research, vol. 303, p 131–133, 1997) and (2S, 3R, 4E)-2-azido-3-O-(tert-butyldiphenylsilyl)-4-octadecene-1,3-diol (compound(3)) represented by the formula (3). The solution is stirred in the presence of a dehydrating agent, e.g., a molecular sieve and the like, at room temperature for about 1 to about 10 hours. The solution is then cooled to about 0° C., and TMSOTf is added thereto. The mixture is stirred at about 0 to about 30° C., preferably at about 0° C., for about 2 to about 24 hours, preferably for about 12 hours, giving the compound (4). In the above procedure, the amounts of the compound (3), dehydrating agent and TMSOTf are not particularly limited, but are preferably selected from the ranges of about 0.5 to about 1.5 moles, about 2 to about 4 moles and about 0.05 to about 0.5 mole, per mole of the compound (2), respectively.

Subsequently, the resulting compound (4) is dissolved in an inert solvent such as benzene. To the solution is added $Ph_3P$, and the mixture is stirred at about 10 to about 40° C., preferably about 30° C., for about 12 to about 96 hours to reduce the azide group of the compound (4) to amino group, giving compound (5). In the above procedure, the amount of $Ph_3P$ is preferably selected from the range of about 1 to about 3 moles per mole of the material compound (4).

The compound (5) can be isolated by conventional methods. In the present invention, the compound (5) can be used in the subsequent reaction as a reaction solution or its concentrate without being isolated.

The subsequent reaction can be carried out by adding stearic acid and a condensing agent WSC, i.e., 1-ethyl-3-(3-dimethylaminopropyl)carbodiimide hydrochloride to the solution of the compound (5) in an appropriate solvent such as the concentrate of the reaction solution, and stirring the mixture at room temperature for about 12 hours, giving a compound (6). In the above procedure, the amounts of stearic acid and the condensing agent (WSC) are preferably selected from the ranges of about 3 to about 5 moles and about 3 to about 5 moles, respectively, per mole of the material compound (5).

The compound (6) can be converted in to a compound (1a) of the invention represented by the formula (1) in which R represents the group (1a) by the following procedure. The compound (6) is dissolved in an appropriate solvent, e.g., methylene chloride and the like. To the solution is added TBAF, and the mixture is stirred at room temperature for about 24 hours to remove a protective group (TBDPS). After being condensed, the reaction mixture is dissolved in methanol. To the solution is added a catalytic amount of sodium methylate, and the mixture is stirred at about 40° C. for about 24 hours. To the mixture is further added water, followed by stirring for about 24 hours to cause hydrolysis and removal of all the protective groups. In the above procedure, the amount of TBAF is preferably selected from about 0.1 to about 1.0 mole per mole of the material compound (6).

The compound of the invention represented by the formula (1) in which R represents the group (1b) can be prepared by the methods shown in the following reaction formulas (II) and (III).

Reaction formula (II)
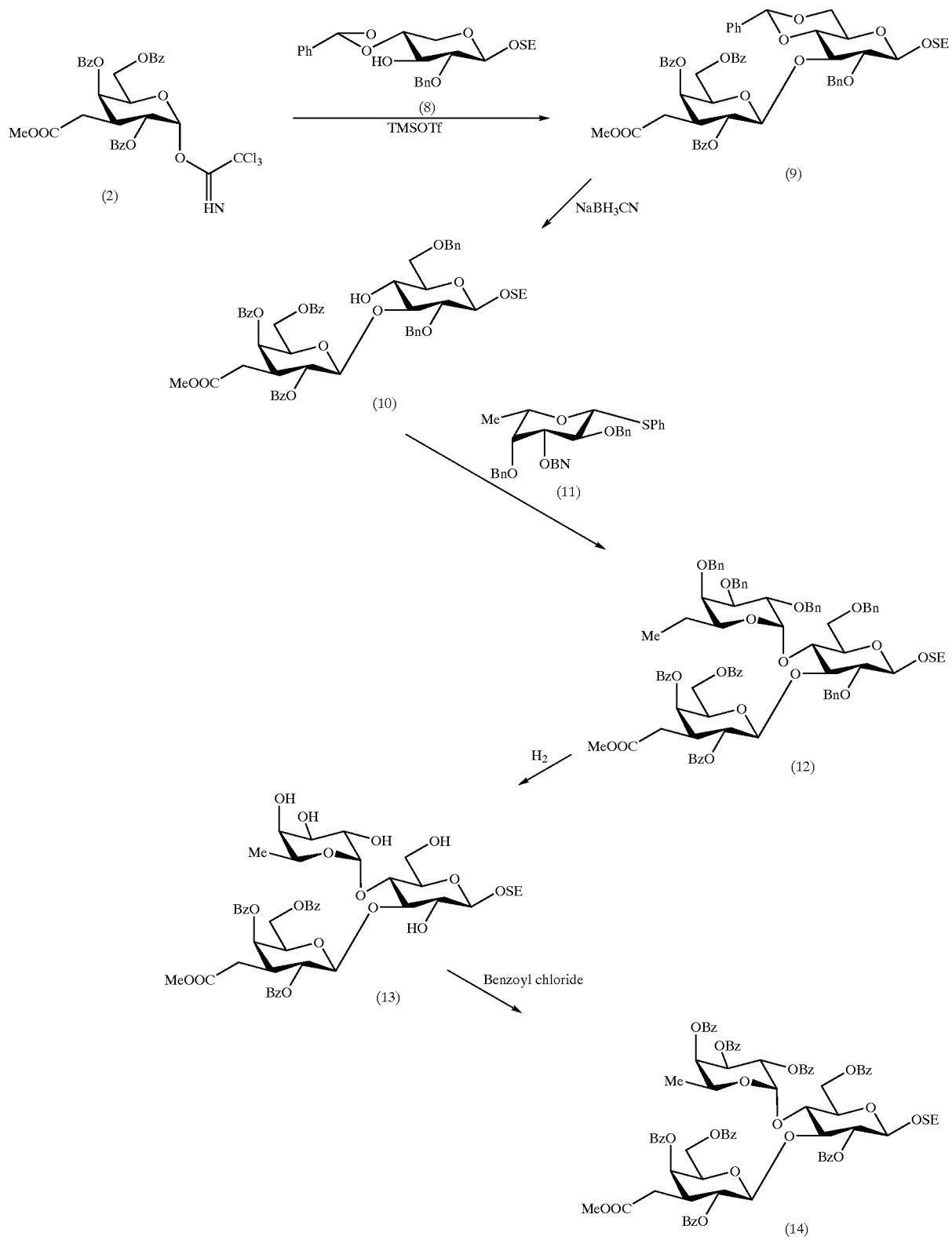
This reaction formula (II) represents the preparation of a compound (14) which is an important intermediate for preparing a compound (1b) of the invention.
In the reaction formula (II), firstly, in a halogenated hydrocarbon solvent such as methylene chloride and the like are dissolved the compound (2) and the known compound (8) (Carbohydrate Research, vol. 303, p 131–133, 1997). The solution is stirred in the presence of an appropriate dehydrating agent, e.g., a molecular sieve and the like, at about room temperature for about 5 hours. Subsequently, the mixture is cooled to about 0° C., and TMSOTf is added to the mixture. The mixture is stirred at about 0 to about 30° C., preferably at about 0° C. for about 2 to about 24 hours, preferably for about 12 hours, giving a compound (9). In the above procedure, the amounts of the compound (8), dehydrating agent and TMSOTf are preferably selected from the ranges of about 1.0 to about 2.0 moles, about 1 to about 3 moles and about 0.05 to about 0.5 mole, per mole of the compound (2), respectively.

Subsequently, the compound (9) is dissolved in an inert solvent, e.g., an ether solvent such as tetrahydrofuran and the like. The solution is stirred in the presence of an appropriate dehydrating agent, e.g., a molecular sieve at room temperature or for about 3 hours, followed by cooling to about 0° C. To the mixture is added $NaBH_3CN$, and the mixture is stirred at room temperature for about 30 minutes to 2 hours, giving a compound (10). In the above procedure, the amounts of the dehydrating agent and $NaBH_3CN$ are preferably selected from about 1 to about 3 moles and about 50 to about 500 moles, respectively, per mole of the material compound (9).

Subsequently, the compound (10) and the known compound (11) (Carbohydrate Research, vol. 303, p 131–133, 1997) are dissolved in an aromatic hydrocarbon solvent, e.g., benzene and the like. To the solution is added TfOH, and the mixture is stirred at about 0 to about 20° C., preferably about 10° C., for about 1 to about 24 hours, usually about 12 hours, giving a compound (12). In the above procedure, the amounts of the compound (11) and TfOH are preferably selected from the ranges of about 1 to about 3 moles and about 0.5 to about 1.5 moles, respectively, per mole of the material compound (10).

The thus obtained compound (12) is dissolved in alcohols, for example, methanol and the like to selectively remove the protective group, i.e., benzyl group, by catalytic reduction method using palladium carbon as a catalyst, giving a compound (13). This catalytic reduction reaction can be carried out by conventional manners, for example, the manner described in Carbohydrate Research, vol.303, p 131–133 (1997).

Further, the compound (13) is dissolved in an appropriate inert solvent, e.g., pyridine and the like. Benzoyl chloride is added to the solution. The mixture is stirred at room temperature for about 3 to about 12 hours, thereby giving a desired compound (14) in which all the hydroxyl groups are protected by benzoyl groups. In the above procedure, the amount of benzoyl chloride is preferably selected from the range of about 10 to about 20 moles per mole of the material compound (13).

By using the thus obtained intermediate compound (14) as a starting material, the compound of the present invention can be prepared in which R is the group (1b) shown in the following reaction formula (III).

Reaction formula (III)

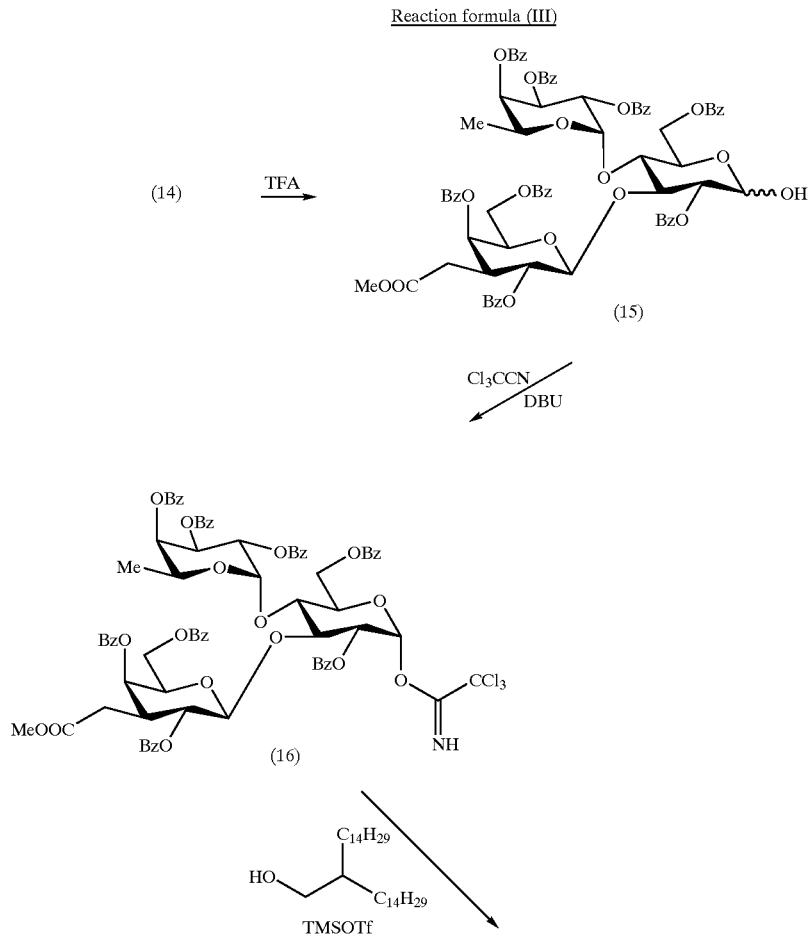

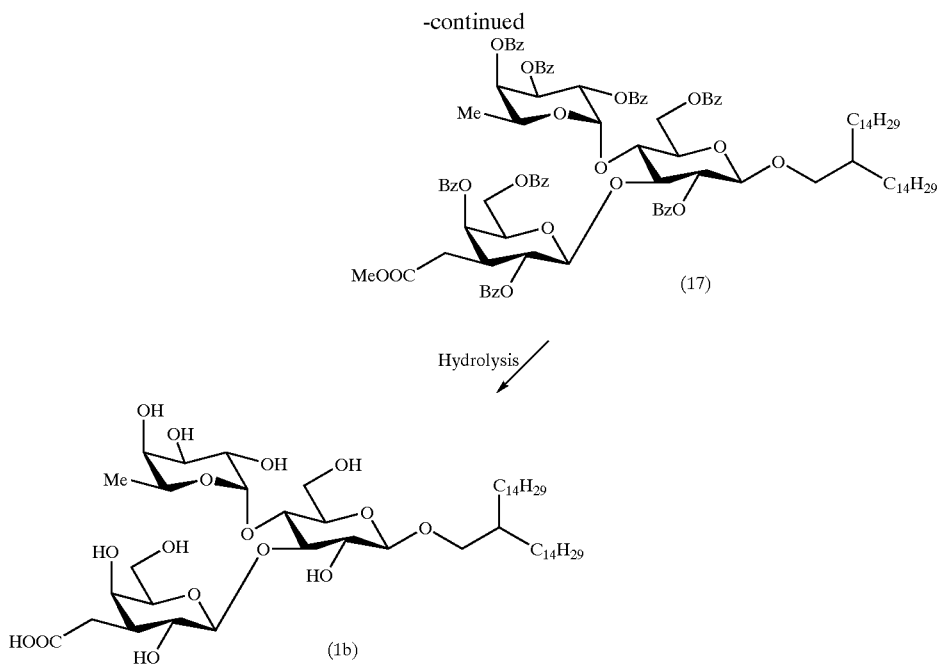

This reaction formula (III) indicates the preparation of the compound (1b) of the present invention from the intermediate compound (14) obtained by the foregoing reaction formula (II).

According to this method, a compound (15) can be prepared by dissolving the compound (14) in methylene chloride and allowing the compound to react with TFA at about 0 to about 10° C., preferably about 0° C. to remove the protective groups (SE) of the compound. In the above procedure, the amount of trifluoroacetic a id is preferably selected from the range of about 1 to about 10 moles per mole of the material compound (14).

The above compound (15) is dissolved in an inert solvent, e.g., methylene chloride and the like, and allowed to react with $Cl_3CCN$ in the presence of DBU, giving a compound (16). In the above procedure, the amounts off DBU and $Cl_3CCN$ are preferably selected from the ranges of about 1 to about 3 moles and about 10 to about 100 moles, respectively, per mole of the material compound (15).

The thus obtained compound (16) and 2-(tetradecyl)-1-hexadecanol are dissolved in methylene chloride, and reacted in the presence of TMSOTf, giving a compound (17). In the above procedure, the amounts of 2-(tetradecyl)-1-hexadecanol and TMSOTf are preferably selected from the ranges of about 1 to about 3 moles and about 1 to about 3 moles, respectively, per mole of the material compound (16).

Finally, the compound (17) is dissolved in methanol. Sodium methylate is added to the solution to cause hydrolysis and removal of the protective groups, thereby giving the compound (1b) of the present invention represented by the formula (1) in which R is the group (1b). In the above procedure, the amount of sodium methylate is preferably selected from the range of about 0.01 to about 0.1 mole, per mole of the material compound (5).

Using the material compound (2), which is described in the reaction formula (I), in place of the compound (16) in the above reaction between the compound (16) and 2-(tetradecyl)-1-hexadecanol, the compound of the invention represented by the formula (1) in which R is the group (1c) can be prepared as shown below in the reaction formula (IV).

Reaction formula (IV)

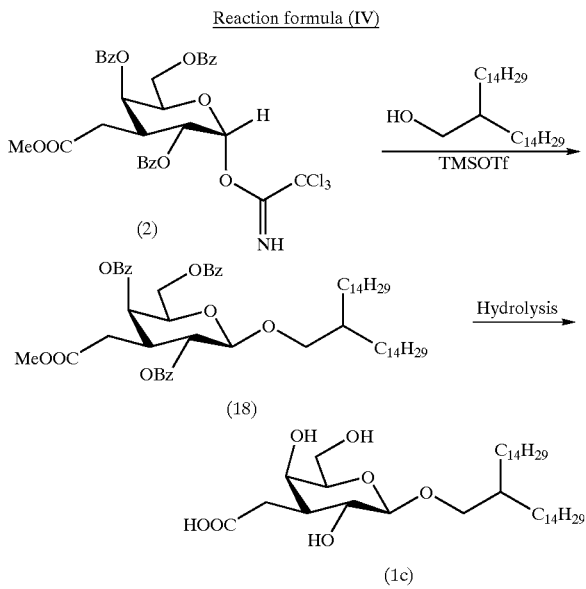

According to the reaction formula (IV), the reaction between the compound (2) and 2-(tetradecyl)-1-hexadecanol is carried out using 2-(tetradecyl)-1-hexadecanol in methylene chloride and like halogenated hydrocarbon solvent in the presence of trimethylsilyl-trifluoromethanesulfonate (TMSOTf). The amount of 2-(tetredecyl)-1-hexadecanol is the range of about 1 to about 10 moles, preferably about 1 to about 3 moles, per mole of the compound (2). TMSOTf is used at an amount between a catalytic amount and an equimolar amount, preferably about 0.1 to about 3 times the molar amount of the compound (2). The reaction completes at temperatures between about 0° C. and room temperature in about 8 to about 24 hours, preferably about 12 hours.

The thus obtained compound (18) is then dissolved in methanol. To the solution is added sodium methylate in a catalytic amount to an approximately equimolar amount, preferably about 0.1 to about 0.2 time the molar amount of the compound (18). The mixture is stirred at about 40° C. for about 24 hours. Water is further added to the mixture. The mixture is stirred for about 24 hours to cause elimination reaction by hydrolysis of all the ester-type protective groups, thereby giving a desired compound (1c) of the present invention represented by the formula (1) in which R is the group (1c).

The compounds of the invention represented by the formula (1) may be converted into pharmaceutically acceptable salts. Examples of such salts include the salts of alkali metals such as sodium, potassium and the like and the salts of alkali earth metals such as calcium, magnesium and the like. The formation reaction of these salts can be carried out by conventional manners.

The desired compounds obtained by the above reaction formulas can be easily isolated and purified by common separating procedures. Examples of such procedures include partition chromatography, preparative thin layer chromatography, recrystallization, solvent extraction and the like.

The compound of the invention has reactivity to selectins such as ELAM-1, GMP-140, LECAM-1 and the like. Hence, the compound of the invention is useful as a ligand which binds to the above selectins for treating and preventing various diseases associated with these selecting, for example, inflammations and cancer metastasis and the like.

Thus, the present invention also provides a pharmaceutical composition which comprises as an active ingredient, the compound of the present invention represented by the formula (1) or a pharmaceutically acceptable salt thereof, together with a pharmaceutically acceptable carrier.

The pharmaceutical composition of the present invention is usually prepared in a general pharmaceutical formulation using the carrier, together with the above active ingredient compound. As the carrier, it may be used various additives commonly used in pharmaceutical preparation depending on the application form (oral administration or parenteral administration) of the preparation. Examples of the additives include excipients, stabilizers, antiseptics, solubilizing agents, fillers, extending agents, binders, humectans, disintegrators, surfactants, lubricants, sweetening agents, colorants, flavoring agents, tonicity modifiers, buffers, antioxidants and the like. These additives may be suitably selected and used depending on the unit dosage form of the obtained preparation.

Although the pharmaceutical composition of the invention is preferably injected intravenously, it may be administered orally, and it can be prepared in a unit dosage form suitable for its administration route. Typical examples of the forms include tablets, pills, powders, fat emulsions, suspensions, granules, capsules, suppositories, injections (liquids, suspensions, etc.), liposomes, ointments and the like.

When the preparation is formed into a tablet, various materials can be used as the carrier. Examples of the carriers include excipients such as lactose, white sugar, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethylcellulose, hydroxypropylcellulose, methylcellulose and polyvinylpyrrolidone; disintegrators such as sodium carboxymethylcellulose, calcium carboxymethylcellulose, hydroxypropylcellulose, dried starch, sodium alginate, agar powder, laminaran powder, sodium hydrogencarbonate and calcium carbonate; surfactants such as polyoxyethylene sorbitan fatty acid ester, sodium lauryl sulfate and stearyl monoglyceride; disintegration inhibitors such as white sugar, stearin, cacao butter and hydrogenated oil; absorption promoters such as quaternary ammonium salt group and sodium lauryl sulfate; humectants such as glycerin and starch; adsorbents such as starch, lactose, kaolin, bentonite and colloidal silicic acid; lubricants such as purified talc, stearate, boric acid powder, polyethylene glycol and the like.

Further, the tablet can be coated with known coatings and prepared as, for example, sugar-coated tablet, gelatin-coated tablets, enteric-coated tablets, film-coated tables, double-layered tablets or multi-layered tablets.

When the pharmaceutical composition of the invention is formed into a pill, it may contain carriers such as glucose, lactose, starch, cacao butter, hydrogenated vegetable oil; kaolin, talc and like excipients; powdered gum arabic, powdered tragacanth, gelatin, ethanol and like binders; laminaran, agar and like disintegrators.

When the pharmaceutical composition of the invention is formed into a suppository, it may use carriers such as polyethylene glycol, cacao butter, higher alcohols, esters of higher alcohols, gelatin, semisynthetic glyceride and the like.

The capsule is prepared by conventional manners, i.e., by mixing the active ingredient compound of the invention with the above-mentioned various carriers and encapsulating the mixture into hard gelatin capsule shells, soft capsule shells and the like.

When the pharmaceutical composition of the invention is prepared as an injection such as a solution, emulsion, suspension and the like, it is preferable that the injection is sterilized and adjusted to be isotonic to human blood. The injection may contain diluents such as water, ethanol, macrogol, propylene glycoli, ethoxylated isostearyl alcohol, polyoxylated isostearyl alcohol, polyoxyethylene sorbitan fatty acid ester and the like. In this case, sodium chloride, glucose, glycerin or the like may be added to the pharmaceutical composition of the invention in an amount sufficient to prepare an isotonic solution. Furthermore, common solubilizers, buffers, soothing agents and the like may be added thereto.

Moreover, the pharmaceutical composition of the invention may contain colorants, preservatives, perfumes, flavoring agents, sweetening agents and other pharmaceuticals, if necessary.

The amount of the compound represented by the formula (1) and its salt (active ingredient compounds) to be added to the pharmaceutical composition of the invention is not limited and may be suitably selected from a wide range. The amount of the active ingredient compounds is usually about 1 to about 70% by weight of the pharmaceutical composition.

A method for administering the above pharmaceutical composition is not particularly restricted, but may be determined depending on the forms of the preparation, the patient's age, sex and other characteristics, severity of disease and the like. For example, tablets, pills, solutions, suspensions, emulsions, granules and capsules are administered orally. Injections are intravenously administered singly or in admixture with common fluid replacement such as glucose, amino acid and the like. The injections may be also administered alone intramuscularly, intracutaneously, subcutaneously or intraperitoneally, where necessary. Suppositories are administered rectally.

The dose of the above pharmaceutical composition is suitably selected depending on its administration method, the patient's age, sex and other factors, severity of disease and the like. The daily dose of the active ingredient is usually about 1 to about 3000 mg per adult per day, and the above dose may be administered once a day or in 2 to 4 divided doses.

BEST MODE FOR CARRYING OUT THE INVENTION

Examples are given below to describe the present invention in more detail. The compound Nos. and abbreviation used below are the same as in Reaction Schemes (I) to (IV).

EXAMPLE 1

Preparation of [2,4,6-tri-O-benzoyl-3-deoxy-3-C-(methoxycarbonylmethyl)-β-D-galactopyranosyl]-(1-1)-(2S,3R,4E)-2-azido-3-O-(tert-butyldiphenylsilyl)-4-octadecene-1,3-diol (4)

The compound (2) (255 mg, 376 μmol) and (2S,3R,4E)-2-azido-3-O-(tert-butyldiphenylsilyl)-4-octadecene-1,3-diol (3) (415 mg, 733 μmol) were dissolved in dichloromethane (2 ml) and stirred in the presence of molecular sieve 4 Å (200 mg) at room temperature for 5 hours, followed by cooling to 0° C. Trimethylsilyltrifluoromethane sulfonate (TMSOTf, 5.7 μl, 30 μmol) was added and the mixture was stirred at 0° C. for 12 hours. After confirming the completion of the reaction using thin layer chromatography (TLC, AcOEt/Hex=1/3) the reaction mixture was filtered through celite and washed with chloroform. The filtrate and the washings were combined and washed with a saturated $Na_2CO_3$ solution and then with $H_2O$. The organic layer was dried over anhydrous $Na_2SO_4$ and concentrated under reduced pressure. The concentrate was subjected to silica gel column chromatography. An amorphous compound (4) (300 mg, 73%) was obtained from the eluate (AcOEt/Hex=1/5).

Elemental analysis: (for $C_{64}H_{77}N_3O_{11}Si$ (1092.42)): Calculated: C,70.37; H,7.10; N,3.85. Found: C,70.35; H,7.02; N,3.55.

$[\alpha]_D^{25}$=−5.7° (C=2.5, $CHCl_3$)

$IRv_{max}$ (film) $cm^{-1}$ 3075–2850(CH) 2100($N_3$) 1750(ester of methyl ester) 1740, 1240(ester of Bz) 710(Ph)

$^1$H-NMR(200 MHz, $CDCl_3$) δ: 1.02(s, 3H, $CH_3CH_2$) 1.27(s, 22H, 11$CH_2$) 2.77–2.90(m, 1H, H-3) 3.44(s, 3H, $COOCH_3$) 4.21(dd, 1H, $J_{5,6a}$=8.6, H-6a) 4.31–4.54(m, 1H, H-6b) 4.61(d, 1H, $J_{1,2}$=7.7, H-1) 4.84–4.95(m, 1H, $J_{5,6b}$=6.8, H-5) 5.36(dd, 1H, H-2) 5.72(near d, 1H, H-4) 7.25–8.16 (m, 30H, 6Ph)

EXAMPLE 2

Preparation of [2,4,6-tri-O-benzoyl-3-deoxy-3-C-(methoxycarbonylmethyl)-β-D-galactopyranosyl]-(1-1)-(2S,3R,4E)-2-octadecanoylamino-3-O-(tert-butyldiphenylsilyl)-4-octadecene-1,3-diol (6)

The compound (4) (300 mg, 274 μmol) was dissolved in benzene (1.5 ml). Water (50 μl) and triphenylphosphine (173 mg, 548 μmol) were added, followed by stirring at 30° C., for 3 days. After confirming the completion of the reaction using TLC (AcOEt/Hex=1/3), the reaction mixture was concentrated under reduced pressure to give a compound (5) as a syrup.

The syrup was dissolved in dichloromethane (3 ml). Stearic acid (231 mg, 822 μmol) and 1-ethyl-3-(3-dimethylaminopropyl)carbodiimide hydrochloride (155 mg, 822 μmol) were added, followed by stirring at room temperature for 12 hours. After confirming the completion of the reaction using TLC (AcOEt/Hex=1/3), the reaction mixture was extracted with chloroform. The organic layer was washed with water and dried over anhydrous $Na_2SO_4$. $Na_2SO_4$ was removed by filtration and the filtrate was concentrated under reduced pressure. The resulting syrup was subjected to silica gel column chromatography. A compound (6) (333 mg, 91%) was obtained from the elute (AcOEt/Hex=1/4).

Elemental analysis: (for $C_{81}H_{113}NO_{12}Si$ (1132.88)) Calculated: C,73.65; H,8.62; N,1.06. Found: C,73.61; H,8.40; N,1.06.

$[\alpha]_D^{25}$=+3.6° (C=4.3, $CHCl_3$)

$IRv_{max}$ (film) $cm^{-1}$ 3450, 3380(NH) 3075–2850(CH) 1750(ester of methyl ester) 1740, 1240(ester of Bz) 1680, 1540(amide) 750, 710(Ph)

$^1$H-NMR(200 MHz, $CDCl_3$) δ: 0.92(d, 6H, $CH_3CH_2$) 1.26(s, 50H, 25$CH_2$) 2.42(t, 2H, $CH_2COOCH_3$) 3.46(s, 3H, $CH_2COOCH_3$) 2.89(m, 1H, H-3) 4.27–4.14(t, 1H, $J_{5,6b}$=6.0, H-6b) 4.28(t, 1H, $J_{5,6a}$=6.6, $J_{gem}$=12.8, H-6a) 4.72(d, 1H, $J_{1,2}$=7.7, H-1) 4.85–4.99(m, 1H, H-5) 5.41(dd, 1H, H-2) 5.76(near d, 1H, H-4) 7.27–8.30(m, 30H, 6Ph)

EXAMPLE 3

Preparation of [3-deoxy-3-C-(carboxymethyl)-β-D-galactopyranosyl]-(1-1)-(2S,3R,4E)-2-octadecanoylamino-4-octadecene-1,3-diol (1a)

The compound (6) (176 mg, 130 μmol) was dissolved in dichloromethane (3 ml), followed by cooling to 0° C. Tetrabutylammonium fluoride (TBAF, 188 μl) was added and the mixture was stirred at room temperature for 24 hours. After confirming the completion of the reaction using TLC (AcOEt/Hex=1/2), the reaction mixture was concentrated under reduced pressure and the residue was dissolved in methanol (5 ml). A catalytic amount of sodium methoxide was added and the mixture was stirred at 40° C. for 24 hours. Further, water was added, followed by stirring for 24 hours. After confirming the completion of the reaction using TLC ($CHCl_3$/MeOH/$H_2O$=5/4/1), the reaction mixture was neutralized with an ion-exchange resin Amberlite IR-120 ($H^+$), followed by removing the resin by filtration. The filtrate and the washings were combined and concentrated under reduced pressure. The resulting syrup was purified by gel filtration (Sephadex LH-20, $CHCl_3$/MeOH/$H_2O$=5/4/0.7) to give a compound (1a) (78 mg, 90%).

Elemental analysis: (for $C_{44}H_{83}NO_9$ (770.15)): Calculated: C,68.62; H,10.86; N,1.82. Found: C,68.41; H,10.66; N,1.65.

$[\alpha]_D^{25}$=−25.0° (C=0.1, $CHCl_3$)

$^1$H-NMR(400 MHz, $CDCl_3$) δ: 0.93(t, 6H, $MeCH_2$) 1.19 (s, 52H, 26$CH_2$) 3.84(d, 1H, $J_{1,2}$=8.79, H-1) 4.01(t, 1H, H-2)

EXAMPLE 4

Preparation of 2-(trimethylsilyl)ethyl O-[2,4,6-tri-O-benzoyl-3-deoxy-3-C-(methoxycarbonylmethyl)-β-D-galactopyranosyl]-(1-3)-2-O-benzyl-4,6-O-benzylidene-β-D-glucopyranoside (9)

The compound (2) (356 mg, 524 μmol) and the compound (8) (313 mg, 682 μmol) were dissolved in dichloromethane (2 ml) and stirred in the presence of molecular sieve 4 Å (600 mg) at room temperature for 5 hours, followed by cooling to 0° C. TMSOTf (10 µl, 52 µmol) was added, followed by stirring at 0° C. for 12 hours. After confirming the completion of the reaction using TLC (AcOEt/Hex=1/2), the reaction mixture was filtered through celite and washed with chloroform. The filtrate and the washings were combined an washed with a saturated $Na_2CO_3$ solution and then with $H_2O$. The organic layer was dried over anhydrous $Na_2SO_4$ and concentrated under reduced pressure. The concentrate was subjected to silica gel column chromatography. A compound (9) (393 mg, 75%) was obtained as syrup from the eluate (AcOEt/Hex=1/4).

Elemental analysis: (for $C_{55}H_{60}O_{15}Si$ (989.14): Calculated: C,66.78; H,6.11. Found: C,66.55; H,6.08.

$[\alpha]_D^{25}$=−18.2° (C=0.7, $CHCl_3$)

$IRv_{max}$ (film) $cm^{-1}$ 3075–2850(CH) 1750(ester of methyl ester) 1740,1240(ester of Bz) 710(Ph)

$^1$H-NMR(400 MHz, $CDCl_3$) δ: 0.84–0.94(m, 2H, $(CH_3)_3$ $SiCH_2CH_2O$) 2.84–2.89(m, 2H, $CH_2COOCH_3$) 2.84–2.89 (m, 1H, H-3 of Glc) 3.35–3.44(m, 2H, $J_{5,6a}$=10.3 Hz, H-2, 5 of Glc) 3.44(s, 3H, $COOCH_3$) 3.17–3.55(m, 1H, $(CH_3)_3$ $SiCH_2CH_2O$) 3.74(t, 1H, $J_{3,4}$=9.15 Hz, H-4 of Glc) 3.80(t, 1H, H-6a of Glc) 3.89–3.95 (m, 1H, $(CH_3)_3SiCH_2CH_2O$) 4.06(t, 1H, H-3 of Glc) 4.10(t, 1H, H-6 of Glc) 4.34–4.38(m, 3H, H-5, 6a, 6b of Gal) 4.44(d, 1H, H-1 of Glc) 4.60(dd, 2H, $CH_2Ph$) 5.20(d, 1H, $J_{1,2}$=7.69 Hz, H-1 of Gal) 5.48(dd, 1H, H-2 of Gal) 5.61(s, 1H, PhCH) 5.72(s, 1H, H-4 of Gal) 7.23–8.15(m, 25H, 5Ph)

EXAMPLE 5

Preparation of 2-(trimethylsilyl)ethyl O-[2,4,6-tri-O-benzoyl-3-deoxy-3-C-(methoxycarbonylmethyl)-β-D-galactopyranosyl]-(1-3)-2,6-di-O-benzyl-β-D-glucopyranoside (10)

The compound (9) (49 mg, 50 µmol) was dissolved in THF (2 ml) and molecular sieve 4 Å was added, followed by stirring for 3 hours. After cooling to 0 ° C., sodium cyanoborohydride (50 mg, 0.75 mmol) was add ed, followed by stirring at room temperature for 30 minutes. After cooling again to 0° C., diethyl ether saturated with hydrochloric acid gas was added dropwise. After confirming the completion of the reaction using TLC (AcOEt/Hex=1/2), the reaction mixture was neutralized with triethylamine. Chloroform and water were added and the reaction mixture was filtered through celite. The filtrate and the washings were combined and concentrated. The resulting syrup was extracted with chloroform and washed with a saturated $Na_2CO_3$ solution and then with $H_2O$. The organic layer was dried over anhydrous $Na_2SO_4$ and concentrated under reduced pressure. The concentrate was subjected to silica gel column chromatography. A compound (10) (59 mg, 70%) was obtained as a syrup from the eluate (AcOEt/Hex=1/3).

Elemental analysis: (for $C_{55}H_{64}O_{14}Si$ (977.199)): Calculated: C,67.60; H,6.60. Found: C,67.46; H,6.40.

$[\alpha]_D^{25}$=+29.8° (C=0.7, $CHCl_3$)

$IRv_{max}$ (film) $cm^{-1}$ 3600–3300(OH) 3075–2850(CH) 1750(ester of methyl ester) 1740, 1240(ester of Bz) 710(Ph)

$^1$H-NMR(400 MHz, $CDCl_3$) δ: 0.83–0.99(m, 2H, $(CH_3)_3$ $SiCH_2CH_2$) 2.46(d, 2H, $CH_2COOCH_3$) 2.94–2.98(m, 1H, $J_{2,3}$=11.71 Hz, $J_{3,4}$=2.56 Hz, H-3 of Gal) 3.30(t, 1H, $J_{1,2,3}$= 7.69 Hz, H-3 of Glc) 3.40(m, 1H, $J_{3,4}$=8.79 Hz, H-5 of Glc) 3.50(s, 3H, $CH_2COOCH_3$) 3.59(t, 1H, H-3 of Glc) 3.65–3.71(m, 1H, $(CH_3)_3SiCH_2CH_2O$) 3.93(dd, 1H, H-3 of Glc) 3.97–4.02(m, 1H, $(CH_3)_3SiCH_2CH_2O$) 4.62(d, 1H, H-1 of Glc) 5.07(d, 1H, $J_{1,2}$=8.06 Hz, H-1 of Gal) 5.54(dd, 1H, H-2 of Gal) 5.77(d, 1H, H-4 of Gal) 7.13–8.19(m, 25H, 5Ph)

EXAMPLE 6

Preparation of 2-(trimethylsilyl)ethyl O-[2,4,6-tri-O-benzoyl-3-deoxy-3-C-(methoxycarbonylmethyl)-β-D-galactopyranosyl]-(1-3)-O-[(2,3,4-tri-O-benzyl-α-L-fucopyranosyl)-(1-4)]-2,6-di-O-benzyl-β-D-glucopyranoside (12)

The compound (10) (33 mg, 30 µmol) and the compound (11) (21 mg, 40 µmol) were dissolved in benzene (1 ml) and stirred in the presence of moleular sieve 4 Å (300 mg) at room temperature for 5 hours, followed by cooling to 0° C. N-iodosuccinimide (NIS, 22.8 mg, 0.10 mmol) and trifluoromethanesulfonic acid (TfOH, 2.4 µl, 27 µmol) were added, followed by stirring at 7° C. for 12 hours. After confirming the completion of the reaction using TLC (AcOEt/Hex=1/2), triethylamine was added to the reaction mixture. The reaction mixture was filtered through celite to remove the insoluble material and washed with chloroform. The filtrate and the washings were combined and washed with a saturated $Na_2CO_3$ solution and then with $H_2O$. The organic layer was dried over anhydrous $Na_2SO_4$ and concentrated under reduced pressure. The resulting syrup was subjected to silica gel column chromatography. An amorphous compound (12) (34 mg, 72%) was obtained from the eluate (AcOEt/Hex=1/4).

Elemental analysis: (for $C_{82}H_{90}O_{19}Si$ (1407.69)): Calculated: C,69.97; H,6.44. Found: C,69.87; H,6.44.

$[\alpha]_D^{25}$=−29.6° (C=0.7, $CHCl_3$)

$IRv_{max}$ (film) $cm^{31\ 1}$ 3075–2850(CH) 1750(ester of methyl ester) 1740, 1240(ester of Bz) 710(Ph)

$^1$H-NMR(400 MHz, $CDCl_3$) δ: 0.86–0.98(m, 2H, $(CH_3)_3$ $SiCH_2CH_2$) 1.61(d, 3H, $CH_3$ of Fuc) 2.48(d, 2H, $CH_2COOCH_3$) 2.87(d, 1H, H-3 of Gal) 3.44(s, 3H, $COOCH_3$) 3.45–3.50(m, 1H, $(CH_3)_3SiCH_2CH_2$) 5.66(d, 1H, H-4 of Gal) 7.14–8.14(m, 40H, 8Ph)

EXAMPLE 7

Preparation of 2-(trimethylsilyl)ethyl O-[2,4,6-tri-O-benzoyl-3-deoxy-3-C-(methoxycarbonylmethyl))-β-D-galactopyranosyl]-(1-3)-O-[α-L-fucopyranosyl-(1-4)]-β-D-glucopyranoside (13)

The compound (12) (234 mg, 166 µmol) was dissolved in methanol (164 ml) and acetic acid (36 ml). Pd-C (234 ml) was added and the mixture was stirred in a stream of hydrogen at room temperature for 6 hours. After confirming the completion of the reaction using TLC (MeOH/$CHCl_3$= 1/5), the reaction mixture was filtered through celite to remove the insoluble material and washed with methanol. The filtrate and the washings were combined and concentrated under reduced pressure. The resulting syrup was subjected to silica gel column chromatography. A compound (13) (119 mg, 82%) was obtained as syrup from the eluate (MeOH/$CHCl_3$=1/20).

Elemental analysis: (for $C_{47}H_{60}O_{19}Si$ (957.06)): Calculated: C,58.98; H,6.32. Found: C,58.78; H,6.27.

$[\alpha]_D^{25}$=−277.6° (C=2.4, $CHCl_3$)

$IRv_{max}$ (film) $cm^{-1}$ 3075–2850(CH) 1750(ester of methyl ester) 1740, 1240(ester of Bz) 710(Ph)

$^1$H-NMR(400 MHz, $CDCl_3$) δ: 0.85–0.98(m, 2H, $(CH_3)_3$ $SiCH_2CH_2$) 1.43(d, 3H, $CH_3$ of Fuc) 2.43(d, 2H, $CH_2COOCH_3$) 2.88(m, 1H, H-3 of Gal) 3.43(s, 3H, $COOCH_3$) 3.38–3.53(m, 1H, $(CH_3)_3SiCH_2CH_2$) 5.00(d, 1H, H-1 of Fuc) 5.68(d, 1H, H-4 of Gal) 7.28–8.12(m, 15H, 3Ph)

EXAMPLE 8

Preparation of 2-(trimethylsilyl)ethyl O-[2,4,6-tri-O-benzoyl-3-deoxy-3-C-(methoxycarbonylmethyl)-β-D-galactopyranosyl]-(1-3)-O-[2,3,4-tri-O-benzoyl-α-L-fucopyranosyl-(1-4)]-2,6-di-O-benzoyl-β-D-glucopyranoside (14)

The compound (13) (120 mg, 125 µmol) was dissolved in pyridine (3 ml). Benzoyl chloride (1.09 ml, 1.01 mmol) was added and the mixture was stirred at room temperature for 12 hours. After confirming the completion of the reaction using TLC (AcOEt/Hex=1/4), the reaction product was concentrated under reduced pressure and diluted with chloroform. The chloroform solution was washed with 1N HCl and them with $H_2O$. The organic layer was dried over anhydrous $Na_2SO_4$ and concentrated under reduced pressure. The resulting syrup was subjected to silica gel column chromatography. An amorphous compound (14)(165 mg, 89%) was obtained from the elute (AcOEt/Hex=1/4).

Elemental analysis: (for $C_{82}H_{80}O_{24}Si$ (1477.60)): Calculated: C,66.66; H,5.46. Found: C,66.53; H,5.37.

$[\alpha]_D^5$=−73.4° (C=1.2, $CHCl_3$)

$IRv_{max}$(film) $cm^{-1}$ 3075–2850(CH) 1750(ester of methyl ester) 1740, 1240(ester of Bz) 710(Ph)

$^1$H-NMR(400 MHz, $CDCl_3$) δ: 0.68–0.82(m, 2H, $(CH_3)_3$SiCH$_2$CH$_2$) 1.50(d, 3H, $CH_3$ of Fuc) 2.54–2.67(m, 2H, $\overline{CH_2}$COOCH$_3$) 2.92–3.00(m, 1H, $J_{3,4}$=2.93, H-3 of Gal) 3.35–3.41(m, 1H, $(CH_3)_3$SiCH$_2\overline{CH_2}$) 3.64(s, 3H, COOCH$_3$) 3.71–3.78(m, 1H, $(CH_3)_3$SiCH$_2\overline{CH_2}$) 4.42(dd, 1H, $J_{1,2,3}$=12.1, H-3 of Glc) 4.47(t, 1H, $\overline{H-2}$ of Glc) 4.56(t, 1H, $J_{5,6}$=6.59, H-5 of Gal) 4.74(d, 1H, H-1 of Fuc) 4.89(d, 1H, H-1 of Glc) 5.16(q, 1H, H-6 of Gal) 5.55(d, 1H, $J_{1,2}$=8.06, H-1 of Gal) 5.62(dd, 1H-2 of Gal) 5.79(d, 1H, H-4 of Gal) 7.38–8.36(m, 40H, 8Ph)

EXAMPLE 9

Preparation of O-[2,4,6-tri-O-benzoyl-3-deoxy-3-C-(methoxycarbonylmethyl)-β-D-galactopyranosyl]-(1-3)-O-[(2,3,4-tri-O-benzoyl-α-L-fucopyranosyl)-(1-4)]-2,6-di-O-benzoyl-β-D-glucopyranoside (15)

The compound (14) (165 mg, 112 μmol) was dissolved in dichloromethane (1 ml), followed by cooling to 0° C. Trifluoroacetic acid (TFA, 1 ml) was added, followed by stirring at room temperature for 1 hour. After confirming the completion of the reaction using TLC (AcOEt/Hex=1/2), ethyl acetate was added while cooling the reaction mixture in an ice bath to decompose the excess reagent. The reaction product was azeotropically distilled with ethyl acetate and extracted with chloroform, followed by washing with a saturated $Na_2CO_3$ solution and then with $H_2O$. The organic layer was dried over anhydrous $Na_2SO_4$ and concentrated under reduced pressure. The concentrate was subjected to silica gel column chromatography. A compound (15) (144 mg, 94%) was obtained as syrup from the eluate (AcOEt/HexL=1/2).

Elemental analysis: (for $C_{77}H_{68}O_{24}$ (1377.37)): Calculated: C,67.15; H,4.98. Found: C,67.11; H,4.89.

$IRv_{max}$ ( film) $cm^{-1}$ 3600–3300(OH) 3075–2850(CH) 1750(ester of methyl ester) 710(Ph)

$^1$H-NMR(400 MHz,$CDCl_3$) δ: 1.50(d, 3H, $CH_3$ of Fuc) 2.23–2.43(m, 2H, CH$_2$COOCH$_3$) 2.73–2.86(m, 2H, H-3 of Gal) 3.32(s, 3H, COOCH$_3$) 5.79(d, 1H, H-4 of Gal) 7.10–8.16(m, 40H, 8Ph)

EXAMPLE 10

Preparation of O-[2,4,6-tri-O-benzoyl-3-deoxy-3-C-(methoxycarbonylmethyl)-β-D-galactopyranosyl]-(1-3)-O-[(2,3,4-tri-O-benzoyl-α-L-fucopyranosyl)-(1-4)]-2,6-di-O-benzoyl-β-D-glucopyranosyl trichloroacetoimidate (16)

The compound (15) (50 mg, 36 μmol) was dissolved in dichloromethane (1 ml), followed by cooling to 0° C.

Trichloroacetonitrile (113 μl, 1.08 mmol) and 1,8-diazabicyclo[5,4,0]-7-undecene (DBU, 2.8 μl, 18 μmol) were added, followed by stirring at 0° C. for 3 hours. After confirming the completion of the reaction using TLC (AcOEt/Hex=1/2), the reaction mixture was subjected to silica gel column chromatography. A compound (16) (55 mg, 93%) was obtained as syrup from the eluate ($CHCl_3$).

Elemental analysis: (for $C_{79}H_{68}O_{24}Cl_3$ (1521.76)): Calculated: C,62.35; H,4.50; NO.92. Found: C,62.11; H,4.24; NO.90.

$[\alpha]_D^{25}$=−35.25° (C=1.2, $CHCl_3$)

$IRv_{max}$(film) $cm^{-1}$ 3350(NH) 3075–2850(CH) 1750(ester of methyl ester) 1740, 1240(ester of Bz) 710(Ph)

$^1$H-NMR(400 MHz, $CDCl_3$) δ: 2.66–2.81(m, 2H, CH$_2$COOCH$_3$) 3.66–3.75(m, 1H, H-3) 3.86(s, 3H, $J_{2,3}$=11.9, COOCH$_3$) 4.73–4.83(m, 2H, $J_{5,6a}$=5.86, H-5, H-6a) 5.07(t, 1H, $J_{5,6b}$=6.0, H-6b) 5.93(dd, 1H, $J_{1,2}$=3.5, H-2) 6.20(near d, 1H, H-4) 7.09(d, 1H, H-1) 7.59–8.47(m, 15H, 3Ph) 8.87(s, 1H, NH)

EXAMPLE 11

Preparation of 2-(tetradecyl)hexadecyl O-[2,4,6-tri-O-benzoyl-3-deoxy-3-C-(methoxycarbonylmethyl)-β-D-galactopyranosyl]-(1-3)-O-[(2,3,4-tri-O-benzoyl-α-L-fucopyranosyl)-(1-4)]-2,6-di-O-benzoyl-β-D-glucopyranoside (17)

The compound (16) (59 mg, 38 μmol) and 2-(tetradecyl)hexadecanol (19 mg, 43 μmol) were dissolved in dichloromethane (1 ml) and stirred in the presence of molecular sieve 4 Å (300 mg) at room temperature for 5 hours, followed by cooling to 0° C. TMSOTf (10 μl, 52 μmol) was added and the mixture was stirred at 0° C. for 12 hours. After confirming the completion of the reaction using TLC (AcOEt/Hex=1/2), the reaction mixture was filtered through celite and washed with chloroform. The filtrate and the washings were combined and washed with a saturated $Na_2CO_3$ solution and, then with $H_2O$. The organic layer was dried over anhydrous $Na_2SO_4$ and concentrated under reduced pressure. The concentrate was subjected to silica gel column chromatography. A compound (17) (393 mg, 75%) was obtained as syrup from the eluate (AcOEt/Hex=1/4).

Elemental analysis: (as $C_{107}H_{128}O_{24}$ (1798.18)) Calculated: C,71.47; H,7.18. Found: C,71.46; H,7.03.

$[\alpha]_D^{25}$=−44.7° (C=0.3, $CHCl_3$)

$^1$H-NMR(400 MHz, $CDCl_3$) δ: 0.90(t, 6H, 2CH$_3$) 1.26(s, 52H, 26CH$_2$) 1.34 (d, 3H, $CH_3$ of Fuc) 2.26–2.40(m, 2H, CH$_2$COOCH$_3$) 2.94–2.97(m, 1H, $J_{3,4}$=2.93, H-3 of Gal) 3.38(s, 3H, COOCH$_3$) 4.69(m, 1H, $J_{4,5}$=5.86, H-5 of Glc) 4.70(d, 1H, $J_{1,2}$=12.1, H-1 of Glc) 4.98(dd, 1H, $J_{2,3}$=7.69, H-3 of Glc) 5.09((m, 1H, H-4 of Glc) 5.18 (dd, 1H, H-2 of Glc) 5.20(d, 1H, $J_{1,2}$=8.06, H-1 of Gal) 5.35(dd, 1H, H-2 of Gal) 5.57(d, 1H, $J_{1,2}$=3.66, H-1 of Fuc) 5.62(dd, 1H, $J_{2,3}$=10.6, H-2 of Fuc) 5.73(dd, 1H, H-4 of Fuc) 6.07 (dd, 1H, H-3 of Fuc) 7.38–8.36(m, 40H, 8Ph)

EXAMPLE 12

Preparation of 2-(tetradecyl)hexadecyl O-[3-deoxy-3-C-(carboxymethyl)-β-D-galactopyranosyl]-(1-3)-O-[α-L-fucopyranosyl-(1-4)]-β-D-glucopyranoside (1b)

The compound (17) (85 mg, 47 μmol) was dissolved in methanol (1 ml) and a catalytic amount of sodium methoxide was added, followed by stirring at 40° C. for 60 hours. After confirming the completion of the reaction using TLC ($CHCl_3$/MeOH/$H_2O$=5/4/1), the reaction mixture was neutralized with an ion-exchange resin Amberlite IR-120 (H⁺). The resin was removed by filtration and washed with methanol. The filtrate and the washings were combined and concentrated under reduced pressure. The resulting syrup was purified by gel filtration (Sephadex LH-20, CHCl$_3$/MeOH/H$_2$O=5/4/0.7) to give a compound (1b) (40 mg, 91%).

Elemental analysis: (for C$_{50}$H$_{94}$O$_{16}$ (951.29)): Calculated: C,63.13; H,9.96. Found: C,62.92; H,9.83.

$[\alpha]_D^{25}$=−33.3° (C=1.0, CHCl$_3$)

$^1$H-NMR(500 MHz, CDCl$_3$) δ: 0.84(t, 6H, 2CH$_3$) 1.24(s, 52H, 26CH$_2$) 1.73(d, 3H, CH$_3$ of Fuc) 4.18(d, 3H, H-1 of Glc) 4.56(d, 1H, H-1 of Gal) 4.82(d, 1H, H-1 of Fuc)

EXAMPLE 13

Preparation of 2-(tetradecyl)hexadecyl 2,4,6-tri-O-benzoyl-3-deoxy-3-C-(methoxycarbonylmethyl)-β-D-galactopyranoside (18)

The compound (2) (111 mg, 163 μmol) and 2-(tetradecyl) hexadecanol (113 mg, 244 μmol) were dissolved in dichloromethane (4 ml) and stirred in the presence of molecular sieve 4 Å (200 mg) at room temperature for 5 hours, followed by cooling to 0° C. TMSOTf (2.6 μl, 13 μmol) was added and the mixture was stirred at 0° C. for 12 hours. After completion of the reaction, the reaction mixture was filtered through celite and washed with chloroform. The filtrate and the washings were combined and washed with a saturated Na$_2$CO$_3$ solution and then with H$_2$O. The organic layer was dried over anhydrous Na$_2$SO$_4$ and concentrated under reduced pressure. The concentrate was subjected to silica gel column chromatography. A compound (18) (158 mg, 95%) was obtained as a syrup from the eluate (AcOEt/Hex=1/10).

Elemental analysis: (for C$_{60}$H$_{80}$O$_{10}$ (969.35)): Calculated: C,74.35; H,9.15. Found: C,74.16; H,9.10.

$[\alpha]_D^{25}$=+14.0° (C=0.9, CHCl$_3$)

IRν$_{max}$(film) cm$^{-1}$ 3075–2850(CH) 1750(ester of methyl ester) 1740, 1240(ester of Bz) 710(Ph)

$^1$H-NMR(200 MHZ, CDCl$_3$) δ: 0.88(t, 6H, 2CH$_3$) 1.23(s, 52H, 26CH$_2$) 2.40–2.59(m, 2H, CH$_2$COOCH$_3$) 2.87–2.92 (m, 1H, H-3) 3.44(s, 3H, CH$_2$COOCH$_3$) 4.15(m, 1H, J$_{5,6}$a= 5.49, H-5) 4.53(t, 1H, J$_{gem}$=11.2, H-6a) 4.64(dd, 1H, H-6b) 4.90(d, 1H, J$_{1,2}$=7.69, H-1) 5.53(dd, 1H, H-2) 5.87(d, 1H, H-4) 7.27–8.30(m, 30H, 6Ph)

EXAMPLE 14

Preparation of 2-(tetradecyl)hexadecyl 3-deoxy-3-C-(carboxymethyl)-β-D-glactopyranoside (1c)

The compound (18) (170 mg, 175 μmol) was dissolved in methanol (5 ml). A catalytic amount of sodium methoxide was added and the mixture was stirred at 40° C. for 24 hours. Further, water was added, followed by stirring for 24 hours. After completion of the reaction, the reaction mixture was neutralized with an ion-exchange resin Amberlite IR-120 (H⁺). The resin was removed by filtration and washed with methanol. The filtrate and the washings were combined and concentrated under reduced pressure. The resulting syrup was purified by gel filtration (Sephadex LH-20, CHCl$_3$/MeOH/H$_2$O=5/4/0.7) to give a compound (1c) (95 mg, 85%).

Elemental analysis: (for (C$_{38}$H$_{74}$O$_7$ (643.00)): Calculated: C,70.98; H,11.60. Found: C,70.92; H,11.49.

$[\alpha]D^{25}$=+61.21° (C=1.87, CHCl$_3$)

$^1$H-NMR(400 MHz, CDCl$_3$) δ: 0.80(t, 6H, 2CH$_3$) 1.19(s, 52H, 26CH$_2$) 3.24(t, 1H, J$_{1,2}$=7.69, H-2) 4.12(d, 1H, H-1)

A test for biological activity of the carboxymethyl galactose derivative of the present invention is described below in detail.

<Binding Inhibitory Activity Test>

The compound (1c) of the present invention obtained in Example 14 (hereinafter referred to as "the compound of the invention") was tested. Used as control compounds were sodium salt of 2-(tetradecyl)hexadecyl 3-O-sulfo-β-D-galactopyranoside (compound 6c described in Chem. Pharm. Bull. 46 (5), pp.797–806 (1998); hereinafter referred to as "comparative compound") and SLe$^x$ (see the same reference).

The binding inhibitory activity of the test compound was measured in terms of the inhibition of binding of premyelocytic leukemia HL-60 cells to immobilized recombinant selectin-IgG fusion proteins by addition of the test compound to the binding reaction system, in accordance with the method described in the above-identified reference.

Stated more specifically, 20 ng of purified P-selectin-IgG was added to each well of a microtiter plate (96 wells, Nunc Maxisorp) and immobilized. Phosphate buffered saline (PBS) was added to each well to make a total volume of 100 μl and the plate was allowed to stand at 4° C. overnight. The excess solution was removed by aspiration, and non-specific binding sites were blocked with PBS containing 1% bovine serum albumin (BSA) at room temperature for 1 hour. After removal of the blocking solution by aspiration, 0.3 mM of the test compound as dissolved in 100 μl of a binding buffer (RPMI1640), and 10$^6$ cells/ml of HL-60 cells as suspended in 100 μl of the binding buffer were added to each well. The plate was centrifuged at 500 rotations per minute for 2 minutes at room temperature, and each well was filled with the binding buffer. The plate was carefully sealed with an adhesive tape so as to avoid trapping any air bubbles. The plate was turned upside down and centrifuged at 500 rotations per minute for 10 minutes to remove unbound HL-60 cells. The adhesive tape was peeled off and the buffer was removed by aspiration. The number of cells bound/well was determined using a cell counting kit (WST-1 assay kit, product of Dojin Kagaku K.K.) (M. Ishiyama. M. Shiga, M. Mizoguchi and P. He, Chem. Pharm. Bull., 41, 1118–1122 (1994)).

The binding inhibition (%) was calculated from the number (M) of bound cells achieved in the test using the test compound and the number (N) of bound cells achieved in the comparative test not using the test compound, according to the following equation:

Binding inhibition (%)=100×(N−M)/N

Using L-selectin-IgG (100 ng) and E-selectin-IgG (40 ng) in place of P-selectin-IgG (20 ng), further tests were carried out in the same manner as above to determine the binding inhibition (%) achieved by the test compound.

Table 1 shows the results (inhibition (%) of binding to the selectins). The data were expressed as an average value of 5 wells±standard error (SE).

TABLE 1

| Binding inhibition (%) | P-selectin | L-selectin | E-selectin |
|---|---|---|---|
| Compound of the invention | 79 ± 3 | 92 ± 3 | 12 ± 8 |
| Comparative compound | 6 ± 3 | 13 ± 3 | 0 ± 5 |
| SLe$^x$ | 3 ± 6 | 0 ± 5 | 0 ± 4 |

Table 1 clearly indicates that the compound of the invention greatly inhibits cell adhesion of the members of a selectin family, as compared with the known sulfathidyl derivative and SLe[x]. The result s reveal that the compound of the invention is effective in preventing and treating inflammations and metastasis of cancers to which the selectin family relates.

What is claimed is:

1. A carboxymethylgalactose derivative represented by the formula (1);

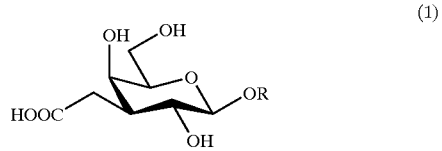

(1)

or a salt thereof, wherein R represents the following group (1a), (1b) or (1c).

(1a)

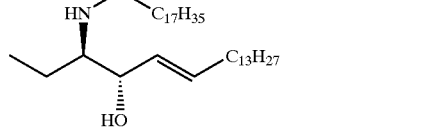

(1b)

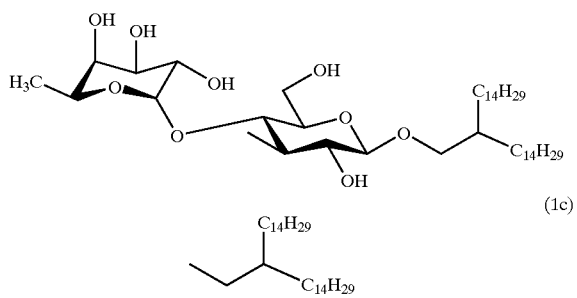

(1c)

2. The carboxymethylgalactose derivative or a salt thereof according to claim 1, wherein R is the group (1a).

3. The carboxymethylgalactose derivative or a salt thereof according to claim 1, wherein R is the group (1b).

4. The carboxymethylgalactose derivative or a salt thereof according to claim 1, wherein R is the group (1c).

5. A pharmaceutical composition comprising, as an active ingredient, at least one member selected from the group consisting of the carboxymethylgalactose derivatives and salts thereof as defined in claim 1, together with a pharmaceutically acceptable carrier.

6. The composition according to claim 5, wherein the active ingredient is selected from the group consisting of the carboxymethylgalactose derivatives and salts thereof as defined in claim 2.

7. The composition according to claim 5, wherein the active ingredient is selected from the group consisting of the carboxymethylgalactose derivatives and salts thereof as defined in claim 3.

8. The composition according to claim 5, wherein the active ingredient is selected from the group consisting of the carboxymethylgalactose derivatives and salts thereof as defined in claim 4.

9. The composition according to any of claims 5–8 which is an inhibitor against cell adhesion of selectin.

10. The composition according to any of claims 5–8 which is an agent for preventing cancer metastasis.

11. The composition according to any of claims 5–8 which is an antiphlogistic.

12. A method for inhibiting cell adhesion of selectin, the method comprising the step of administering, to a patient, an effective amount of at least one active ingredient selected from the group consisting of the carboxymethylgalactose derivatives and salts thereof as defined in claim 1.

13. The method according to claim 12, wherein the active ingredient is selected from the group consisting of the carboxymethylgalactose derivatives and salts thereof as defined in claim 2.

14. The method according to claim 12, wherein the active ingredient is selected from the group consisting of the carboxymethylgalactose derivatives and salts thereof as defined in claim 3.

15. The method according to claim 12, wherein the active ingredient is selected from the group consisting of the carboxymethylgalactose derivatives and salts thereof as defined in claim 4.

16. A method for inhibiting cell adhesiveness of selection, the method comprising the step of administering, to a patient, an effective amount of the pharmaceutical composition as defined in claim 5.

17. The method according to claim 16, wherein the pharmaceutical composition is the composition as defined in claim 6.

18. The method according to claim 16, wherein the pharmaceutical composition is the composition as defined in claim 7.

19. The method according to claim 16, wherein the pharmaceutical composition is the composition as defined in claim 8.

20. A method for preventing cancer metastasis comprising administering, to a patient who requires cancer metastasis prevention, an effective amount of at least one active ingredient selected from the group consisting of the carboxymethylgalactose derivatives and salts thereof as defined in claim 1.

21. The method according to claim 20, wherein the active ingredient is selected from the group consisting of the carboxymethylgalactose derivatives and salts thereof as defined in claim 2.

22. The method according to claim 20, wherein the active ingredient is selected from the group consisting of the carboxymethylgalactose derivatives and salts thereof as defined in claim 3.

23. The method according to claim 20, wherein the active ingredient is selected from the group consisting of the carboxymethylgalactose derivatives and salts thereof as defined in claim 4.

24. A method for preventing cancer metastasis by administering, to a patient who requires cancer metastasis prevention, an effective amount of the pharmaceutical composition as defined in claim 5.

25. The method according to claim 24, wherein the pharmaceutical composition is the composition as defined in claim 6.

26. The method according to claim 24, wherein the pharmaceutical composition is the composition as defined in claim 7.

27. The method according to claim 24, wherein the pharmaceutical composition is the composition as defined in claim 8.

28. A method for inhibiting inflammation of a patient comprising administering, to the patient, an effective amount of at least one active ingredient selected from the group consisting of the carboxymethylgalactose derivatives and salts thereof as defined in claim 1.

29. The method according to claim 28, wherein the active ingredient is selected from the group consisting of the carboxymethylgalactose derivatives and salts thereof as defined in claim 2.

30. The method according to claim 28, wherein the active ingredient is selected from the group consisting of the carboxymethylgalactose derivatives and salts thereof as defined in claim 3.

31. The method according to claim 28, wherein the active ingredient is selected from the group consisting of the carboxymethylgalactose derivatives and salts thereof as defined in claim 4.

32. A method for inhibiting inflammation of a patient comprising administering an effective amount of the pharmaceutical composition according to claim 5 to the patient.

33. The method according to claim 32, wherein the pharmaceutical composition is the composition as defined in claim 6.

34. The method according to claim 32, wherein the pharmaceutical composition is the composition as defined in claim 7.

35. The method according to claim 32, wherein the pharmaceutical composition is the composition as defined in claim 8.

* * * * *